US00PP34187P2

(12) United States Plant Patent
Bradford et al.

(10) Patent No.: US PP34,187 P2
(45) Date of Patent: May 3, 2022

(54) 'PEARL PRINCESS VIII'

(50) Latin Name: *Prunus persica*
Varietal Denomination: Pearl Princess VIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,915

(22) Filed: Dec. 17, 2021

(51) Int. Cl.
*A01H 6/74* (2018.01)
*A01H 5/08* (2018.01)

(52) U.S. Cl.
USPC ..... Plt./195

(58) Field of Classification Search
USPC ..... Plt./195
See application file for complete search history.

(56) References Cited

U.S. PATENT DOCUMENTS

PP17,282 P2 12/2006 Bradford
PP18,771 P2 4/2008 Bradford

*Primary Examiner* — Annette H Para

(57) ABSTRACT

The present invention relates to a new and distinct variety of peach tree, *Prunus persica*, broadly characterized by a large size, vigorous, hardy, self-fertile, productive and regular bearing tree. The variety blooms during early to mid season and requires about 450 chilling hours. The fruit matures under the ecological conditions described in late May, with first picking on May 25, 2021. The fruit is uniform, large in size, oblate in shape, clingstone in type, firm in texture, mostly red in skin color, white in flesh color, and sub-acidic in flavor.

1 Drawing Sheet

Botanical classification: *Prunus persica.*
Variety denomination: 'PEARL PRINCESS VIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess VIII'.

In 2010 we gathered early maturing fruit from several different trees that all had 'May Princess' (U.S. Plant Pat. No. 18,771) peach as a common parent. Their seeds were removed, cracked, stratified, germinated, and grown as seedlings on their own root in our greenhouse with the label '12G873 (P2)'. Upon reaching dormancy the seedlings were transplanted as a group to a cultivated area of our experimental orchard located near Le Grand, Calif., in Merced County (San Joaquin Valley). During the fruit evaluation season of 2015, we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its known grandparent, 'May Princess' peach (U.S. Plant Pat. No. 18,771), by having a large tree, by being self-fertile, by having a large flower, by having reniform leaf glands, and by producing peaches that are mostly red in skin color, clingstone in type, oblate in shape, and firm in texture, but is quite distinguished therefrom by producing peaches that are white instead of yellow in flesh color, that are sub-acidic instead of acidic in flavor, and that ripen about sixteen days later.

The present variety is most similar to 'Ivory Duchess' peach tree (U.S. Plant Pat. No. 17,282), by having a vigorous tree, by blooming in the early season, by having large blossoms, by being self-fertile, by having a bitter kernel, and by producing white flesh peaches that are clingstone in type, mostly red in skin color, firm in texture, and sub-acidic in flavor, but is distinguished therefrom by producing peaches that are oblate instead of globose in shape, that are larger in size, that are sweeter, and that mature about four days earlier.

SUMMARY OF VARIETY

In summary, the present peach variety is characterized by a large size, vigorous, hardy, self-fertile, productive and regular bearing tree. The variety blooms during early season and requires about 350 chilling hours. The fruit matures under the ecological conditions described in late May, with first picking on May 25, 2021. The fruit is uniform, large in size, oblate in shape, clingstone in type, firm in texture, mostly red in skin color, white in flesh color, and sub-acidic in flavor.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 1, 2021, on the original tree during its eleventh growing season. The blossom and flower descriptions were made the previous blooming season. All major color code designations are by reference to the Inter-Society Color Council, National Bureau of Standards. Common color names are also used occasionally.

PARENTAGE

Seed parent: Unnamed seedling of 'May Princess' (U.S. Plant Pat. No. 18,771) peach.
Pollen parent: Self-pollinated.

TREE

Size: Large, reaching and maintaining a height of 12' [3.66 m.] and a spread of 11' [3.35 m.] after eleven growing seasons utilizing typical dormant pruning.
Vigor: Vigorous, responding typically to irrigation and fertilization. The variety grows about 2' [0.61 m.] of surplus top-growth during the spring and summer. The plant should be grown on a standard commercial rootstock for production purposes.
Growth: Spreading and dense.
Form: Pruned to vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 350 hours.
Leaf bud burst: Early, just after the start of flowering.
Trunk:
- *Size*.—Slender, reaching a maximum diameter of 6" [152 mm.] after the eleventh growing season.
- *Texture*.—Rough to shaggy.
- *Bark color*.—A Brownish gray [64. brGy] and Light brownish gray [63. l.brGy] variegation with Dark grayish brown [62. d.gy.Br] crevices present.
- *Lenticels*.—Approximate Number Per Square Inch: 8. Color: Dark orange yellow [72. d.OY]. Average Size: ⅜" [9.5 mm.] in length. The width is typically one fourth as much as the length. Shape: Elongated.

Branches:
- *Size*.—Medium, diameter of main scaffold is 3¼" [69.9 mm.] measured 12" above the crotch, diameter of the limb is 2¼" [57.2 mm.] measured 12" above the first fork.
- *Texture*.—Smooth to medium on first and second year wood, increasing roughness with age.
- *Color*.—1st Year Wood Topside: Grayish red [19. gy.R]. 1st Year Wood Underside: Brilliant yellow green [116. brill.YG]. Older Wood: A light grayish yellowish brown [79. l.gy.yBr] and Grayish yellowish brown [80. gy.yBr] variegation.
- *Lenticels*.—Number Per Square Inch: About 30 on second year wood. Color: Strong yellowish brown [74. s.yBr]. Average Size: Small, 1/16" [1.6 mm.] in length. The width is typically one fourth as much as the length. Shape: Elongated.

Leaves:
- *Size*.—Large. Average Length: 6½" [165.1 mm.]. Average Width: 1¾" [44.5 mm.].
- *Arrangement*.—Alternate.
- *Thickness*.—Medium.
- *Form*.—Elliptical.
- *Apex*.—Acuminate.
- *Base*.—Rounded to acute with an average base angle of 75 degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Vein color*.—Light yellow green [119. l.YG].
- *Petiole*.—Average Length: 7/16" [11.1 mm.]. Average Thickness: 1/16" [1.6 mm.]. Color: Light yellow green [119. l.YG].
- *Stipules*.—Number: Typically two per leaf, up to six per growing tip. Average Length: ¼" [6.4 mm.]. Color: Vivid yellow green [115. v.YG] becoming Dark brown [59. d.Br] with maturity.
- *Glands*.—Number: 2 to 4 per leaf. Position: Alternate, positioned on the petiole near the base of blade. Form: Reniform. Size: Medium, about 1/16" [1.6 mm.] in length.
- *Leaf buds*.—Pointed.

Flower buds:
- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Pale purplish pink [252. p.pPk].

Flowers: Perfect, complete, perigynous, usually a single pistil, about thirty stamens, five sepal and petal locations alternately positioned.
- *Type*.—Showy, large.
- *Average flower diameter*.—1⅞" [47.6 mm.].
- *Average flower depth*.—⅜" [9.5 mm.] when fully open.
- *Number of petals*.—Five, extra petal fragments rarely observed, double blossoms not observed.
- *Petal arrangement*.—Overlapping.
- *Petal shape*.—Oval.
- *Petal margin*.—Entire, slightly wavy.
- *Average petal diameter*.—⅝" [15.9 mm.].
- *Average petal length*.—¾" [19.1 mm.].
- *Petal apex*.—Rounded.
- *Petal base*.—Rounded.

*Petal color*.—Light purplish pink [249. l.pPk] toward the apex and Moderate purplish red [258. m.pR] toward the base on both sides.
*Anthocyanin coloration intensity*.—Moderate.
*Anther color*.—Strong red [12. s.R] surrounding a Light yellow [86. l.Y] center at bloom onset.
*Pollen*.—Anthers produce an abundance of Brilliant yellow [83. brill.Y] pollen.
*Stigma color*.—Brilliant yellow [83. brill.Y].
*Stigma position*.—Typically located slightly above the nearby anthers.
*Stamen position*.—Typically located about 1/16" [1.6 mm] below the petals.
*Average pistil length*.—13/16" [20.6 mm.].
*Average stamen length*.—9/16" [14.3 mm.].
*Ovary*.—Pubescent.
*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—3/8" [9.5 mm.].
*Sepal width*.—1/4" [6.4 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Early, blooms at the same time as 'May Princess' (U.S. Plant Pat. No. 18,771) peach.
*Onset of bloom*.—One percent on Feb. 11, 2021.
*Date of full bloom*.—Feb. 21, 2021.
*Duration of bloom*.—One to two weeks, dependent on ambient temperature.
*Bloom density*.—Heavy.
*Number per cluster*.—1 to 3 with single flowers most common.

FRUIT

Maturity when described: Firm ripe, Jun. 1, 2021.
Date of first picking: May 25, 2021.
Date of last picking: Jun. 7, 2021.
Size: Fairly uniform, large.
*Average diameter axially*.—2 3/4" [69.9 mm.].
*Average diameter across suture plane*.—3 1/4" [82.6 mm.].
*Average diameter across cheek plane*.—3 5/16" [84.1 mm.].
*Typical weight*.—9.3 ounces [265 grams].
Form: Uniform, oblate, symmetrical.
*Longitudinal section form*.—Oblate.
*Axial view*.—Round.
Suture: Extends from the stem cavity, along the sides, and ends with a slight depression just beyond the pistil point.
*Near the base*.—A very shallow groove.
*Along the side*.—A very shallow trough with some stitching.
*Near the apex*.—A shallow groove.
Ventral surface: Rounded.
Lips: Lightly lipped toward the apex, fairly equal on most.
Cavity: Flaring, Pale yellow green [121. p.YG] stem markings typical.
*Depth*.—9/16" [14.3 mm.].
*Breadth*.—1 1/4" [31.8 mm.].
Base: Truncate.
Apex: Rounded, slightly cordate if viewed parallel to the suture.
Pistil point: Apical, negligible in length, Light yellow [86. y.Y] on the tip, depressed within the suture.
Stem: Medium.
*Average length*.—3/8" [9.5 mm.].
*Average width*.—3/16" [4.8 mm.].
Skin:
*Thickness*.—Medium.
*Surface*.—Pubescent.
*Density of the pubescence*.—Medium.
*Down*.—Very short, does not roll up when rubbed.
*Tenacity*.—Tenacious to flesh.
*Astringency*.—Non-astringent.
*Tendency to crack*.—None observed.
*Color*.—Very deep red [14. v.deep R] over a Light yellowish pink [28. l.yPk] background with very minor Light yellow [86. l.Y] freckling toward the apex.
Flesh:
*Color*.—Yellowish white [92. yWhite] with a slight amount of Light pink [4. l.Pk] streaking.
*Surface of pit cavity*.—Covered with Yellowish white [92. yWhite] fibers when twisted from the stone.
*Amygdalin*.—Scare.
*Juice*.—Abundant.
*Texture*.—Firm and crisp.
*Fibers*.—Few and fine.
*Ripens*.—Fairly even, slightly earlier at the apex.
*Flavor*.—Sweet and sub-acidic, typically 17 brix.
*Aroma*.—Moderate.
*Eating quality*.—Very good.

STONE

Type: Clingstone.
Form: Oval.
Hilum: Narrow.
Base: Truncated.
Apex: Rounded to acute.
Sides: Fairly equal.
Tip: Sharp, about 1/8" [3.2 mm.] in length.
Surface: Irregularly furrowed near the apex, pitted toward the base.
Ridges: Rounded.
External color: Light yellowish brown [76. l.yBr].
Pit wall color when cracked: Pale orange yellow [73. p.OY].
Cavity surface color: Light orange yellow [70 l.OY].
Average pit wall thickness: 1/4" [6.4 mm.].
Average length: 1 5/16" [33.3 mm.].
Average width: 1" [25.4 mm.].
Average breadth: 3/4" [19.1 mm.].
Tendency to split: None observed.
Kernel:
*Form*.—Oval.
*Skin color*.—Pale yellow [89. p.Y] when first removed.
*Pellicle color*.—Dark olive brown [96. d.OlBr].
*Vein color*.—Grayish yellow [90. gy.Y].
*Taste*.—Bitter.
*Viable*.—Yes.
*Average length*.—5/8" [15.9 mm.].

*Average width.*—½" [12.7 mm.].

*Amygdalin.*—Abundant.

USE

Market: Fresh market and long distance shipping.

Keeping quality: Good, fruit quality observed to remain in good condition after 17 days in standard cold room at 36° Fahrenheit [2° Celsius].

Shipping quality: Good.

Resistance to insects: Not tested.

Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described.

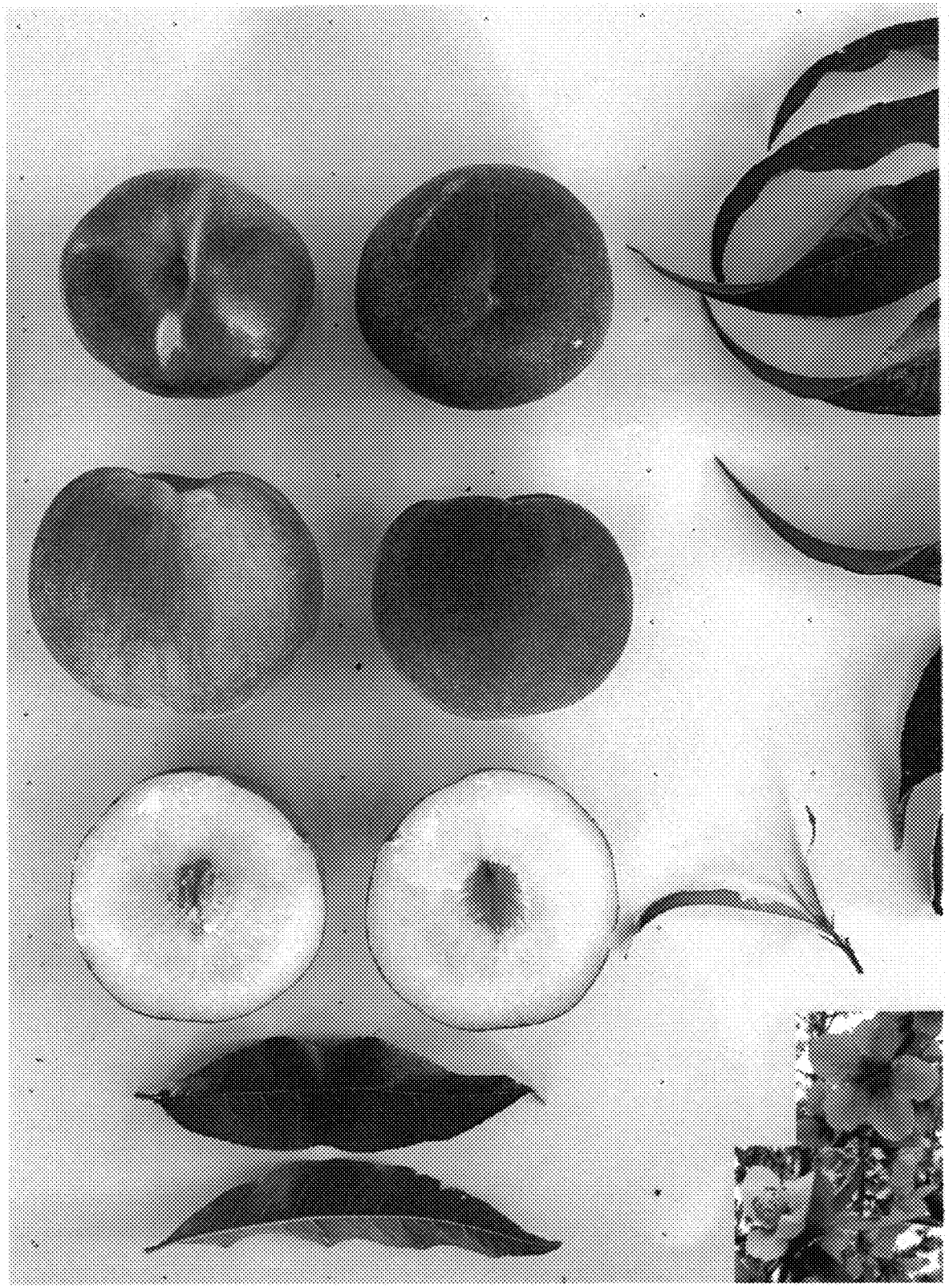

* * * * *